US009458512B2

(12) United States Patent
Colaizzi et al.

(10) Patent No.: US 9,458,512 B2
(45) Date of Patent: Oct. 4, 2016

(54) KIT FOR THE DETECTION OF BED BUGS

(76) Inventors: Ernest Colaizzi, Dallas, TX (US); Ryan Smith Westberry, Denver, CO (US)

( * ) Notice: Subject to any disclaimer, the term of this patent is extended or adjusted under 35 U.S.C. 154(b) by 107 days.

(21) Appl. No.: 13/540,162

(22) Filed: Jul. 2, 2012

(65) Prior Publication Data

US 2013/0011836 A1   Jan. 10, 2013

Related U.S. Application Data

(60) Provisional application No. 61/504,594, filed on Jul. 5, 2011.

(51) Int. Cl.
*C12Q 1/68* (2006.01)

(52) U.S. Cl.
CPC ... *C12Q 1/6888* (2013.01); *G01N 2333/43552* (2013.01)

(58) Field of Classification Search
USPC ........................................................ 435/6.11
See application file for complete search history.

(56) References Cited

U.S. PATENT DOCUMENTS

| | | | | |
|---|---|---|---|---|
| 6,439,069 | B1* | 8/2002 | Cates | 73/865.8 |
| 6,625,922 | B1* | 9/2003 | Ernsberger, IV | 43/122 |
| 7,093,389 | B1* | 8/2006 | Meier et al. | 43/107 |
| 7,743,552 | B2* | 6/2010 | Borth et al. | 43/131 |
| 2003/0050470 | A1* | 3/2003 | An | C07H 21/00 536/24.3 |
| 2011/0138678 | A1* | 6/2011 | Smith | 43/107 |

FOREIGN PATENT DOCUMENTS

| | | | | |
|---|---|---|---|---|
| CN | 101503741 | * | 8/2009 | C12Q 1/70 |
| CN | 101676407 | * | 3/2010 | C12Q 1/70 |

OTHER PUBLICATIONS

Szalanski AL, Austin JW, McKern JA, Steelman CD, Gold RE. Mitochondrial and ribosomal internal transcribed spacer 1 diversity of Cimex lectularius (Hemiptera: Cimicidae). J Med Entomol. 2008. 45(2):229-36.*
Szalanski AL, Tripodi AD, Austin JW. Multiplex polymerase chain reaction diagnostics of bed bug (Hemiptera: Cimicidae). J Med Entomol. 2011. 48(4):937-40.*
Szalanski AL, Austin JW, McKern JA, Steelman CD, McCoy T, Miller, DM. Time Course Analysis of bed bug, Cimex lectularius L., (Hemiptera: Cimicidae) Blood meals with use of polymerase chain reaction.. J Agric. Urban Entomol. 2006. 23(4):237-41.*
Szalanski et al. Molecular Diagnostics of the Formosan Subterranean Termite (Isoptera: Rhinotermitidae). Florida Entomol. 2004. 87(2):145-151.*

(Continued)

*Primary Examiner* — Samuel Woolwine (57) ABSTRACT

A kit and method for the detection of bed bugs is discussed. The kit comprises at least one pair of polymerase chain reaction ("PCR") amplification primers capable of forming a Cimicidae-DNA-amplification-product for a family of organisms of a Cimicidae. Additionally, the kit provides a specimen collection device for collecting a DNA sample from an area suspected of harboring one or more members of the Cimicidae family. The kit also provides a DNA probe having fluorescent primer chemistry. In a preferred embodiment, the nucleic acid amplification detection kit utilized a pair of PCR primers. The probe utilizes fluorescent primer chemistry and contains chemistry similar to Taqman Probes, Molecular Beacons, Hybridization Probes; or Eclipse Probes. Additionally, the kit contains a positive-control-Cimicidae DNA template for confirming Cimicidae-DNA-amplification-product.

7 Claims, 6 Drawing Sheets

(56) References Cited

OTHER PUBLICATIONS

Rychlik W, Rhoads RE. A computer program for choosing optimal oligonucleotides for filter hybridization, sequencing and in vitro amplification of DNA. Nucleic Acids Res. 1989. 17(21):8543-51.*
GenBank Accession No. EU126968 for the Cimex lectularius 18S rRNA gene, partial sequence; ITS1 (complete); and 5.8S rRNA, gene partial sequence. Mar. 11, 2008 [online], [retrieved on Feb. 11, 2013], retrieved from the Internet: <URL: www.ncbi.nlm.nih.gov/nuccore/eu126968>.*
GenBank Accession No. GU985548 for the Cimex lectularius isolate 16S rRNA gene, partial sequence; mitochondrial. Apr. 27, 2010 [online], [retrieved on Feb. 11, 2013], retrieved from the Internet: <URL: www.ncbi.nlm.nih.gov/nuccore/gu985548>.*
Jothikumar N, da Silva AJ, Moura I, Qvarnstrom Y, Hill VR. Detection and differentiation of Cryptosporidium hominis and Cryptosporidium parvum by dual TaqMan assays. J Med Microbiol. 2008. 57(Pt 9):1099-105.*
Wetmur JG. DNA probes: applications of the principles of nucleic acid hybridization. Crit Rev Biochem Mol Biol. 1991;26(3-4):227-59. Review.*
Zhang T, Fang HH. Applications of real-time polymerase chain reaction for quantification of microorganisms in environmental samples. Appl Microbiol Biotechnol. 2006. 70(3):281-9. Epub Feb. 10, 2006 Review.*
Hartman LJ, Coyne SR, Norwood DA. Development of a novel internal positive control for Taqman based assays. Mol Cell Probes. 2005. 19(1):51-9. Epub Dec. 10, 2004.*
Heid CA, Stevens J, Livak KJ, Williams PM. Real time quantitative PCR. Genome Res. 1996. 6(10):986-94.*
Machine Translation of CN 101503741 provided in English (done on Feb. 15, 2013) with Chinese Patent office—plain text web translation tool <http://www.chinatrademarkoffice.com/index.php/ptsearch>.*
Afonina IA, Reed MW, Lusby E, Shishkina IG, Belousov YS. Minor groove binder-conjugated DNA probes for quantitative DNA detection by hybridization-triggered fluorescence. Biotechniques. Apr. 2002; 32(4):940-949.*
SantaLucia Jr, John. Physical principles and visual-OMP software for optimal PCR design. PCR Primer Design. Humana Press, 2007:pp. 3-33.*

* cited by examiner

KIT FOR THE DETECTION OF BED BUGS

RELATED APPLICATIONS

This application claims priority to U.S. Provisional Patent Application, Ser. No. 61/504,594 titled "Kit For the Detection of Bed Bugs" filed on Jul. 5, 2011, having Ernie Colaizzi, et al., listed as inventors, the entire content of which is hereby incorporated by reference.

FEDERALLY SPONSORED RESEARCH

No federal funds were used in the development of the present invention.

JOINT RESEARCH AGREEMENTS

Not Applicable.

SEQUENCE LISTING

The NCBI Accession Number for the Internal Transcribed Spacer 1 is EU126968. Using SEQ ID No.: 1 and SEQ ID No.: 2 the Amplicon size is 92 base pairs.

```
                                       SEQ ID No. 1
Forward primer       5'-3' TCGCATTGACCGCGTAG.

SEQ ID No. 2
Reverse primer       5'-3' ACGGTACTTCGGACGGA.

SEQ ID No. 3
Fluorescent Probe    5'-3' TGTGGACCCAGGCCGTCCGA.
```

The NCBI Accession number for the 16s Ribosomal RNA Gene is GU985548.1. Using SEQ ID No.: 4 and SEQ ID No.: 5 the Amplicon size is 319 bp.

```
                                       SEQ ID No. 4
   (forward primer for Cimicidae organisms)
   5'-3' CTGTGCAAAGGTAGCATAATAA.

SEQ ID No. 5
   (reverse primer for Cimicidae organisms)
   5'-3' CCTTAAGTAACTTAAACTTATAATCAAAAC.
```

BACKGROUND

The current invention is a kit and method for the detection of bed bugs. The kit comprises at least one pair of polymerase chain reaction ("PCR") amplification primers capable of forming a Cimicidae-DNA-amplification-product for a family of organisms of a Cimicidae. Additionally, the kit provides a specimen collection device for collecting a DNA sample from an area suspected of harboring one or more members of the Cimicidae family. The kit also provides a DNA probe having fluorescent primer chemistry. In a preferred embodiment, the nucleic acid amplification detection kit utilized a pair of PCR primers. The probe utilizes fluorescent primer chemistry and contains chemistry similar to commercially trademarked products, including: TAQMAN PROBES, MOLECULAR BEACONS, HYBRIDIZATION PROBES; OR ECLIPSE PROBES. Additionally, the kit contains a positive-control-Cimicidae DNA template for confirming Cimicidae-DNA-amplification-product.

Bed Bugs.

There are many species of insects that feed on warm-blooded animals. Bed bugs are small parasitic insects that prefer human blood. The name "bed bug" is derived from the insect's preferred habitat of houses and especially beds or other areas where people sleep. Bed bugs have been shown to hide in small nooks and crevices during the day, only appearing at night in order to feed on the sleeping human host.

Bed bugs are also known by a variety of names including wall louse, mahogany flat, crimson rambler, heavy dragoon, chinche and redcoat. Epidemiologists skilled in the art have shown that a number of human health effects may occur due to bed bugs including skin rashes, emotional responses, allergic reactions and infections. A current diagnosis of bed bugs involves both finding bed bugs and the occurrence of compatible symptoms.

Although not wanting to be bound by theory, the bed bug known as *Cimex lectularius* is the species best adapted to human environments. It is found in temperate climates throughout the world. *C. lectularius* may have originated in the Middle East, in caves inhabited by bats and humans. Other species include *Cimex hemipterus*, found in tropical regions, which also infests poultry and bats, and *Leptocimex boueti*, found in the tropics of West Africa and South America, which infests bats and humans. *Cimex pilosellus* and *Cimex pipistrella* primarily infest bats, while *Haematosiphon inodora*, a species of North America, primarily infests poultry.

Bed bugs were mentioned in literature of ancient Greece as early as 400 BC, and mentioned specifically by Aristotle. Pliny's Natural History, first published circa 77 AD in Rome, claimed bed bugs had medicinal value in treating ailments such as snakebites and ear infections. The belief in the medicinal use of bed bugs persisted until at least the 18th century, when Guettard recommended their use in the treatment of hysteria. Bed bugs were first mentioned in Germany around the 11 th century, in France in the 13th century and in England in 1583, though they remained rare in England until 1670. Some in the 18th century believed bed bugs had been brought to London with supplies of wood to rebuild the city after the Great Fire of London (1666). Giovanni Antonio Scopoli noted their presence in Carniola (roughly equivalent to present-day Slovenia) in the 18th century.

Although bed bugs have been known as human parasites for thousands of years, bed bugs were largely eradicated as pests in the early 1940's in most of the developed world due to the use of DDT. In contrast, the prevalence of bed bug bites and related conditions has been increasing since about 1995. Several reasons have been postulated, but none have been proven, for example:
  Increased foreign travel;
  Increased purchases of second-hand furnishings;
  Increased focus on controlling other pests;
  Neglecting bed bug countermeasures; and
  Increased resistance of bed bugs to pesticides.

In general, bug bites can be embarrassing and uncomfortable, however, the bigger danger comes from bed bugs harboring diseases that may be transmitted during an infestation. It is well known that other types of bug bites cause very serious diseases. For example, *Yersinia pestis* is a type of bacteria that causes the Bubonic plague throughout certain parts of the world. Plague transmission from infected animals generally occurs in one of three ways: (i) bites from infected rodent fleas; (ii) direct contact with infected tissue or bodily fluids; (iii) inhaling infected flea fecal droplets.

Bites from infected fleas accounts for about 85 percent of the human cases of bubonic plague transmission.

Bites from bed bugs from the Cimicosis family may lead to a range of skin manifestations from no visible effects to prominent blisters. Diagnosis involves both finding bed bugs and the occurrence of compatible symptoms. Treatment involves the elimination of the insect. Bed bugs can cause a number of health effects including skin rashes, psychological effects and allergic symptoms, additionally, bed bugs can be infected by at least 28 human pathogens. No study has found clearly that the bed bug insect bites are capable of transmitting a pathogen directly to a human being. Because bed bugs have been found with Methicillin-Resistant *Staphylococcus Aureus* ("MRSA") and with vancomycin-resistant *Enterococcus faecium* ("VRE"), there is still fear that such pathogens can be transmitted to humans. If a connection between bed bug bites and human pathogen transmission is firmly established, such infected bed bugs could spread the drug-resistant bacteria to the community at large.

Adult bed bugs are reddish-brown, flattened, oval and wingless. Bed bugs have microscopic hairs that give them a banded appearance. Adults grow to 4-5 mm in length and 1.5-3.0 mm wide and can be seen with the naked eye. Newly hatched nymphs are translucent, lighter in color and become browner as they molt and reach maturity. Bed bugs may be mistaken for other insects such as booklice and carpet beetles, or vice-versa, which is one reason to correctly identify a bed bug infestation. Bed bugs are nocturnal and difficult to visually detect during the day.

Common Locations of Bed Bug Infestations.

The thin and flat nature of bed bugs bodies allow them to hide in cracks and crevices. They often will congregate in locations within a dwelling that are shielded from sunlight, including but not limited to the seams and inside cushioning of mattresses and chairs, supporting frames for beds, and baseboards. Although bed bugs can hide individually, they are social creatures and more often will congregate in groups.

Size of Bed Bug Infestations.

Some pest control professionals have deemed light infestations to be anything below 200 bed bugs in a residence; a medium infestation can be in the range of 200-300 bed bugs in a residence; and severe infestations can be as bad as 2,000-3,000 bed bugs in a single residence. With the recent reemergence of bed bugs in the developed world, hotels and other establishments that provide short-term lodging are at constant risk of infestations. This is especially concerning when bed bugs can be transferred from an infested residence or hotel room through suitcases.

Detection of Bed Bug Infestations.

The current detection methods for bed bugs are visual. For example, a diagnosis of bed bugs is confirmed typically by catching one and identifying it correctly together with symptoms of human bite marks. An indirect method of identification is black tracks on bedding, which are the bed bugs' fecal stains. (The stains show up best on white- or light-colored bedding, and may be more difficult to see on darker bedding.) When crushing kills a recently fed bed bug, the result is a blood smear on whatever surface they were crushed. Crushing them also will produce a unique sickly sweet scent, which can also be detected when a dwelling is severely infested.

Bed bugs can also be detected by their unique bite pattern of a linear group of three, sometimes referred to as a "breakfast, lunch, and dinner" pattern. Red welts can appear on the skin of people after a bed bug has fed. Bed bugs have an anesthetic in their saliva so the victim does not feel the bite when it feeds. In contrast, an allergic reaction can take place leaving an itchy welt when the victim wakes up in the morning. Some people do not have an immune response to bed bugs, showing no welts post-feeding. The effects of these bites on humans varies from person to person, but often produce welts and swelling that are more itchy and longer-lasting than mosquito bites. Some people, however, have little or no reaction. If an individual is awake in the middle of the night, a flashlight can be run up and down a mattress or bedding to attempt to locate active bugs. Some experts have suggested this technique because the physical vibrations of getting up from the mattress and turning on a room light may give bed bugs sufficient time to retreat to hiding places, making detection more difficult.

The surest sign of bed bugs is to see or capture an actual bed bug. Bed bugs tend to hide close to beds, and in tufts, seams and crevices in mattresses and bed frames. They may also hide in surrounding furniture, in piles of books or papers, in carpeting, in linens, in electrical outlets or under peeling wallpaper. Visual inspection of these areas can uncover bed bugs if present. Adult bed bugs look like apple seeds: they have flat copper-colored bodies and are about ¼ inch in length. When a bed bug feeds, its body swells and becomes bright red. Young bed bugs are very small, approximately 1/16 inch in length. Although Bed bugs can live for up to a year and can survive months without feeding, they normally try to feed every five to ten days.

Several more sophisticated methods for monitoring and detecting bed bugs have been used in the past. For example, U.S. Pat. No. 7,591,099, titled "Bed Bug Monitor," issued to Lang, et al., on Sep. 22, 2009 describes an insect monitoring and trapping device that includes a base and a lid for covering the base, and is constructed to provide a trap interior and an insect opening for insects to access the trap interior. The device includes a heating device provided within the trap interior for attracting insects, and an adhesive surface provided within the trap for trapping insects. The entire content of this U.S. patent is hereby incorporated by reference.

U.S. Pat. No. 7,743,552, titled "Bed bug Detection, Monitoring and Control Techniques," issued to Borth, et al., on Jun. 29, 2010 and describes one non-limiting variation of a detection arrangement includes one or more sensors each structured to detect at least one biochemical substance indicative of biochemistry of one or more target insect species and provide a corresponding sensor signal, a controller responsive to the sensor signal of each of the one or more sensors to determine if the one or more insect species are present and generate a corresponding output signal, and an indicator responsive to the output signal to indicate the presence of the one or more insect species. The entire content of this U.S. patent is hereby incorporated by reference.

Eradication of Bed Bugs.

Once a bed bug infestation is detected in a home or hotel, swift treatment of the problem is advised to help prevent the problem from spreading to different rooms or units in a building. Female bed bugs can lay more than 200 eggs in their lifetime; they can live for weeks to months without feeding. Moreover, bed bugs can travel more than 100 feet on their own, spreading from room to room on clothing, luggage and bedding. Early detection of an infestation is believed to be a key component to controlling it.

Commercial insecticides (usually pyrethroids) are applied as spot treatments to cracks and crevices where bed bugs are hiding. Increased penetration of the insecticide into cracks and crevices can be achieved if accumulated dirt and debris are first removed using a vacuum cleaner. Many readily available aerosol pesticide sprays will cause bed bugs to scatter making eradication more difficult. Dust formulations may be used to treat wall voids and attics. Repeat insecticide applications are recommended/required if bed bugs are present two weeks after the initial treatment, as it is difficult to find all hiding places and hidden eggs may have hatched Eradication of bed bugs frequently requires a combination of pesticide and non-pesticide approaches. Pesticides that have historically been effective include: pyrethroids, dichlorvos and malathion. Resistance to pesticides has increased significantly over time and there are concerns of negative health effects from their continued use. Mechanical approaches such as vacuuming the insects and heat-treating or wrapping mattresses have been recommended.

The carbamate insecticide propoxur is highly toxic to bed bugs. However, in the United States the Environmental Protection Agency (EPA) has been reluctant to approve indoor use because of its potential toxicity to children after chronic exposure. Bed bugs are developing resistance to various pesticides including DDT and organophosphates. Some populations have developed a resistance to pyrethroid insecticides. Now often ineffective, the resistance to pyrethroids allows for new chemicals that work in different ways to be investigated, thus chemical management can continue to be one aspect to resolving bed bug infestations. There is growing interest in both synthetic pyrethroid and the pyrrole insecticide, chlorfenapyr. Insect growth regulators, such as hydroprene (Gentrol), are also sometimes used.

Bed bug populations in Arkansas have been found to be highly resistant to DDT, with an LD50 of more than 100,000 ppm. Studies conducted in Africa showed that DDT made bed bugs more active. Bed bug pesticide-resistance appears to be increasing dramatically. Bed bug populations sampled across the U.S. showed a tolerance for pyrethroids several thousands of times greater than laboratory bed bugs. New York City bed bugs have been found to be 264 times more resistant to deltamethrin than Florida bed bugs due to nerve cell gene mutation.

A population genetics study of bed bugs in the United States, Canada, and Australia using a mitochondrial DNA marker found high levels of genetic variation. This suggests the studied bed bug populations did not undergo a genetic bottleneck as one would expect due to insecticide control during the 1940s and 1950s, but instead, that populations may have been maintained on other hosts such as birds and bats. In contrast to the high amount of genetic variation observed with the mitochondrial DNA marker, no genetic variation in a nuclear RNA marker was observed. This suggests increased gene flow of previously isolated bed bug populations, and given the absence of barriers to gene flow, the spread of insecticide resistance may be rapid.

Traditional methods of repelling and/or killing bed bugs include the use of plants, fungi, and insects (or their extracts), such as black pepper, black cohosh (*Actaea racemosa*), *Pseudarthria hookeri, Laggera alata, Eucalyptus saligna* oil, henna (*Lawsonia inermis* or *camphire*), "infused oil of *Melolontha vulgaris*" (presumably cockchafer), fly agaric (*Amanita muscaria*), *Actaea* spp. (e.g. black cohosh), tobacco, "heated oil of *Terebinthina*" (i.e. true turpentine), wild mint (*Mentha arvensis*), narrow-leaved pepperwort (*Lepidium ruderale*), *Myrica* spp. (e.g. bayberry), Robert geranium (*Geranium robertianum*), bugbane (*Cimicifuga* spp.), "herb and seeds of *Cannabis*", "*opulus*" berries (possibly maple or European cranberrybush), masked hunter bugs (*Reduvius personatus*), "and many others." In the mid-19th century, smoke from peat fires was recommended.

Silt-sized material-dusts have been used to ward off insects from grain storage for centuries, including "plant ash, lime, dolomite, certain types of soil, and diatomaceous earth (DE) or Kieselguhr". Of these, diatomaceous earth in particular has seen a revival as a nontoxic (i.e. in amorphous form) residual pesticide for bed bug abatement. Insects exposed to diatomaceous earth may take several days to die.

Basket-work panels were put around beds and shaken out in the morning, in the UK and in France in the 19th century. Scattering leaves of plants with microscopic hooked hairs around a bed at night, then sweeping them up in the morning and burning them, was a technique reportedly used in southern Rhodesia and in the Balkans. Prior to the mid-twentieth century, bed bugs were very common. According to a report by the UK Ministry of Health, in 1933 there were many areas where all the houses had some degree of bed bug infestation." Bed bugs were a serious problem during World War II. General MacArthur commented that bed bugs are the "greatest nuisance insect problem . . . at bases in the U.S."

With the arrival of potent pesticides, famously DDT in the 1940s, bed bugs almost disappeared in western countries. Recently, bed bug infestations have resurged for reasons that are not clear, but contributing factors may be complacency, increased resistance, bans on pesticides and increased international travel. The current wave of bed bug infestations across America has spawned an industry for bed bug prevention, eradication, detection and reporting of infestations.

One skilled in the art appreciates that the bed bug detection kit and method used thereof can be a lower cost, and more effective alternative to early detection of bed bugs when compared to many other current methods used today. Additionally, the skilled artisan understands that many types of modifications can be made to the method without departing from the scope and spirit of the invention.

SUMMARY

One aspect of the current invention is a bed bug detection kit. The kit comprises at least one pair of polymerase chain reaction ("PCR") amplification primers capable of forming a Cimicidae-DNA-amplification-product for a family of organisms of a Cimicidae. Additionally, the kit provides a specimen collection device for collecting a DNA sample from an area suspected of harboring one or more members of the Cimicidae family. The kit also provides a DNA probe having fluorescent primer chemistry. In a preferred embodiment, the nucleic acid amplification detection kit utilized a pair of PCR primers having a DNA sequences with at least 95% similarity to SEQ ID 1 and SEQ ID 2. In a second preferred embodiment, the probe having the fluorescent primer chemistry with at least 95% similarity to SEQ ID 3 and contains probe-based chemistry similar to TAQMAN PROBES, MOLECULAR BEACONS, HYBRIDIZATION PROBES; OR ECLIPSE PROBES. In a third preferred embodiment, the nucleic acid amplification detection kit also contains a positive-control-Cimicidae DNA template for confirming Cimicidae-DNA-amplification-product.

A second aspect of the current invention is a method for determining the presence of a bed bug in a test sample. The method comprises hybridizing DNA in the test sample with at least one oligonucleotide probe having (SEQID No.: 3), wherein the oligonucleotide probe being conjugated to a signal generating compound is capable of producing a detectable signal, and determining the presence of the bed bug by detecting the signal generated.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Terms

Before describing the present invention in detail, it is to be understood that this invention is not limited to particular compositions or composition delivery systems, which may vary. One having ordinary skill in the art will understand that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive. In describing and claiming the present invention, the following terminology will be used in accordance with the definitions set out below.

It must be noted that, as used in this specification and the appended claims, the singular forms "a," "an" and "the" include plural referents unless the context clearly dictates otherwise. Thus, for example, reference to "a pharmacologically active agent" includes a mixture of two or more such compounds, reference to "a base" includes mixtures of two or more bases, reference to "an acid" includes mixtures of two or more acids, and the like.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. A nucleic acid comprising a functional biological equivalent of the sequence primers described herein are primers that have been engineered to contain distinct nucleic acid sequences while simultaneously a similar gene or gene region of a DNA template.

The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Restriction enzymes are used to ensure plasmid integrity and correctness.

The term "fluorescent primer chemistry" or "probe-based chemistry" as used herein refers to Real-Time PCR Chemistries, wherein many fluorescent primer- and probe-based chemistries have been devised and are available from different commercial vendors, wherein the "fluorescent primer" or "probe-based" chemistries may be known under trademarked names, including: TAQMAN PROBES; MOLECULAR BEACONS; HYBRIDIZATION PROBES; ECLIPSE PROBES; AMPLIFLUOR ASSAYS; SCORPIONS PRIMERS; LUX PRIMERS; AND QZYME PRIMERS.

The term "Swab" as used herein, comprises a dry sterile polysesther, nylon, Dacron, or cotton swab/sponge having a single tip on a wood, metal, or plastic handle or functional equivalent thereof. The preferred swab will be usually relatively long, about six inches and be free from DNA contamination or compounds/chemicals that would interfere with PCR amplification of the selected species' DNA. These often are packaged sterile, one or two to a paper or plastic sleeve. One advantage of the sleeve and the handle may be that the package can be autoclaved to be sterilized (plastic sleeves or handles would melt in the autoclave). However, one of ordinary skill in the art understands that a collection swab may have any type of material capable of binding sample DNA to be used subsequently for PCR amplification has been contemplated without departing from the scope and spirit of the invention. The term "swab" can also be a sample of dust, particulate matter, filter debris from vacuum or collection device.

The term "Suspect Surface," as used herein includes, but is not limited to a mattress, bed sheets, bed frame, bed covers, floor surface, desk, nightstand, pillows, areas close to beds, and in tufts, seams and crevices in mattresses, surrounding furniture, in piles of books or papers, in carpeting, in linens, in electrical outlets or under peeling wallpaper, storage boxes and the like. One having ordinary skill in the art will appreciate that any surface capable of holding or hiding bed bugs or bed bug DNA has been contemplated as a "suspect surface" without departing from the scope and spirit of the invention.

METHODS

Nucleic Acid Amplification.

In one aspect, the invention provides methods for amplifying a nucleic acid molecule, comprising subjecting the nucleic acid molecule to an amplification reaction in an amplification reaction mixture comprising a DNA polymerase.

Nucleic acid molecules may be amplified according to any of the literature-described manual or automated amplification methods. As used herein "amplification" refers to any in vitro method for increasing the number of copies of a nucleotide sequence with the use of a DNA or RNA polymerase. In one embodiment, nucleic acid amplification results in the incorporation of nucleotides into a DNA molecule or primer, thereby forming a new DNA molecule complementary to a nucleic acid template. The formed DNA molecule and its template can be used as templates to synthesize additional DNA molecules. As used herein, one amplification reaction may consist of many rounds of DNA replication. DNA amplification reactions include, for example, polymerase chain reactions ("PCR"). One PCR reaction may consist of 10 to 100 "cycles" of denaturation and synthesis of a DNA molecule. Such methods include, but are not limited to, PCR (as described in U.S. Pat. Nos. 4,683,195 and 4,683,202, which are hereby incorporated by reference), Strand Displacement Amplification ("SDA") (as described in U.S. Pat. No. 5,455,166, which is hereby incorporated by reference), and Nucleic Acid Sequence-Based Amplification ("NASBA") (as described in U.S. Pat. No. 5,409,818, which is hereby incorporated by reference). For example, amplification may be achieved by a rolling circle replication system which may even use a helicase for enhanced efficiency in DNA melting with reduced heat (see Yuzhakou et al., "Replisome Assembly Reveals the Basis for Asymmetric Function in Leading and Lagging Strand Replication," Cell 86:877-886 (1996) and Mok et al., "The *Escherichia coli* Preprimosome and DnaB Helicase Can Form Replication Forks That Move at the Same Rate," J. Biol. Chem. 262:16558-16565 (1987), which are hereby incorporated by reference). Most preferably, nucleic acid molecules are amplified by the methods of the present invention using PCR-based amplification techniques.

In a preferred embodiment, the amplification reaction involves a high temperature denaturation step, and the DNA polymerase used is a thermostable polymerase. Preferred temperatures for the high temperature denaturation step range from about 90° C. to about 98° C., with temperatures from 93° C. to 94° C. being especially preferred. Such preferred amplification reactions include thermocycling amplification reactions, such as polymerase chain reactions involving from about 10 to about 100 cycles, more preferably from about 25 to about 50 cycles, and peak temperatures of from about 90° C. to about 98° C., more preferably 93° C. to 94° C. In a preferred embodiment, the DNA polymerase used in an amplification reaction is derived from *Thermus aquaticus*.

In a preferred embodiment, the amplification reaction mixture used in amplification reactions involving one or more high temperature denaturation steps, as described and exemplified more fully herein.

Any source of nucleic acid, in purified or nonpurified form, can be utilized as the starting nucleic acid, if it contains or is thought to contain the target nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction using the same or different primers may be so utilized. The nucleic acid amplified is preferably DNA. The target nucleic acid sequence to be amplified may be only a fraction of a larger molecule or can be present initially as a discrete molecule, so that the target sequence constitutes the entire nucleic acid. The starting nucleic acid may contain more than one desired target nucleic acid sequence which may be the same or different. Therefore, the method is useful not only for producing large amounts of one target nucleic acid sequence, but also for amplifying simultaneously multiple target nucleic acid sequences located on the same or different nucleic acid molecules.

Any specific (i.e., target) nucleic acid sequence can be produced by the present methods. It is only necessary that a sufficient number of bases at both ends of the target sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater the specificity of the primers for the target nucleic acid sequence, and, thus, the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code can be used for each strand. One primer from this collection will be homologous with the end of the desired sequence to be amplified.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

The target nucleic acid sequence is amplified by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° C. to 105° C., preferably about 90° C. to about 98° C., still more preferably 93° C. to 94° C., for times ranging from about 1 to 10 minutes If the original nucleic acid containing the sequence to be amplified is single stranded, its complement is synthesized by adding oligonucleotide primers thereto. If an appropriate single primer is added, a primer extension product is synthesized in the presence of the primer, a two-component polymerase, and the four nucleotides described below. The product will be partially complementary to the single-stranded nucleic acid and will hybridize with the nucleic acid strand to form a duplex of unequal length strands that may then be separated into single strands, as described above, to produce two single separated complementary strands.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally, it occurs in a buffered aqueous solution, most preferably at a pH of about 8.5 to 8.9. Notably the preferred pH range differs from the preferred pH ranges of Pol I enzymes. Preferably, a molar excess (for cloned nucleic acid, usually about 1000:1 primer:template, and for genomic nucleic acid, usually about 106:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Nucleoside triphosphates, preferably dATP, dCTP, dGTP, and dTTP are also added to the synthesis mixture in adequate amounts, and the resulting solution is preferably heated to a temperature from about 90° C.-95° C. for about 1 to 10 minutes, preferably from 15 sec to 2 minutes. After this heating period, the solution is allowed to cool to a temperature of about 60° C., which is preferable for the primer hybridization. The two component polymerase then performs nucleic acid synthesis at a temperature well above room temperature, preferably at a temperature from about 60° C. to 75° C.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional polymerase, nucleotides, and primers may be added if necessary for the reaction to proceed under the conditions described above. Again, the synthesis will be initiated at one end of the oligonucleotide primers and will proceed along the single strands of the template to produce additional nucleic acids.

The steps of strand separation and extension product synthesis can be repeated as often as needed to produce the desired quantity of the specific nucleic acid sequence. The amount of the specific nucleic acid sequence produced will increase in an exponential fashion.

The present invention can be performed in a step-wise fashion where after each step new reagents are added, or simultaneously, wherein all reagents are added at the initial step, or partially step-wise and partially simultaneously, wherein fresh reagent is added after a given number of steps.

Kits.

In other preferred embodiments, the invention provides kits for use in nucleic acid amplification of Beg Bugs as disclosed herein.

A nucleic acid amplification kit according to the present invention comprises a thermostable DNA polymerase, reaction buffer, and dNTPs. The amplification kit encompassed by this aspect of the present invention may further comprise additional reagents and compounds necessary for carrying out standard nucleic acid amplification protocols (See U.S. Pat. Nos. 4,683,195 and 4,683,202, which are directed to methods of DNA amplification by PCR).

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Construction of DNA Primers and Methods of Detection

A Kit for Polymerase Chain Reaction ("PCR") Identification of Bed Bugs.

The present invention utilizes a DNA amplification technique known as PCR to amplify a specific region of the genome from organisms of the Cimicidae family from residual DNA samples left by the bed bug life cycle (e.g. eggs, exoskeleton, fecal matter, and other biological samples). The process of general PCR was first described in U.S. Pat. No. 4,683,202, titled "Process for amplifying nucleic acid sequences," issued to Kary Mullis on Jul. 28, 1987 describing a process for amplifying any desired specific nucleic acid sequence contained in a nucleic acid or mixture thereof. The process comprises treating separate complementary strands of the nucleic acid with a molar excess of two oligonucleotide primers, and extending the primers to form complementary primer extension products that act as templates for synthesizing the desired nucleic acid sequence. The steps of the reaction may be carried out stepwise or simultaneously and can be repeated as often as desired. The entire content of this U.S. patent is hereby incorporated by reference.

Flourescent Probe PCR is the preferred method of detecting bed bugs with this invention. Early detection of bed bugs from organisms of the Cimicidae family may be important in preventing a localized bed bug problem from growing into multi-room infestations. The present invention comprises a Bed Bug DNA Detection kit having: (a) at least one pair of polymerase chain reaction ("PCR") amplification primers capable of forming a Cimicidae-DNA-amplification-product for a family of organisms of a Cimicidae; (b) a specimen collection device for collecting a DNA sample from an area suspected of harboring one or more members of the Cimicidae family; and (c) a positive-control-Cimicidae DNA template for confirming Cimicidae-DNA-amplification-product. The use of a Cimicidae DNA binding probe technology can be utilized either in conjunction or alternatively to the PCR amplification primers.

The PCR primers were designed using a combination of software:
1) Integrated DNATechnology (ITD) OligoAnalyzer software
   a. IDT—1710 Commercial Park Coralville, Iowa 52241
2) The mFold Web Server
   a. The RNA Institute, College of Arts and Sciences, University at Albany, State University of New York One having ordinary skill in the art understands that Primer- and probe-based detection chemistries share some common features. In general, these chemistries use some form of fluorescence quenching to ensure that specific fluorescence is detected only when the product of interest is amplified. The primer or target-specific oligonucleotide probe is labeled with a reporter fluorophore, but in most cases, fluorescence is quenched when the specific target is not detectable. Usually this is accomplished by attaching a quencher molecule to the primer or probe, and devising some mechanism by which the reporter and quencher are separated when the primer or probe binds to its specific target.

In real-time PCR, fluorescent primers and probes offer two main advantages over DNA-binding dyes. First, they specifically detect the target sequence so nonspecific products do not affect the accuracy of quantification. Second, they allow multiplex reactions to be performed.

TAQMAN Probes.

TAQMAN assays include a sequence-specific, fluorescently labeled oligonucleotide probe called a TAQMAN probe, in addition to the sequence-specific primers. Also known as 5'-nuclease assays, TAQMAN assays exploit the 5'-exonuclease activity of certain thermostable polymerases, such as Taq or Tth. The TAQMAN probe is labeled with a fluorescent reporter at the 5' end and a quencher at the 3' end. A commonly used fluorescent reporter-quencher pair is fluorescein (FAM, which emits green fluorescence) and Black Hole Quencher 1 dye.

Figure 5:
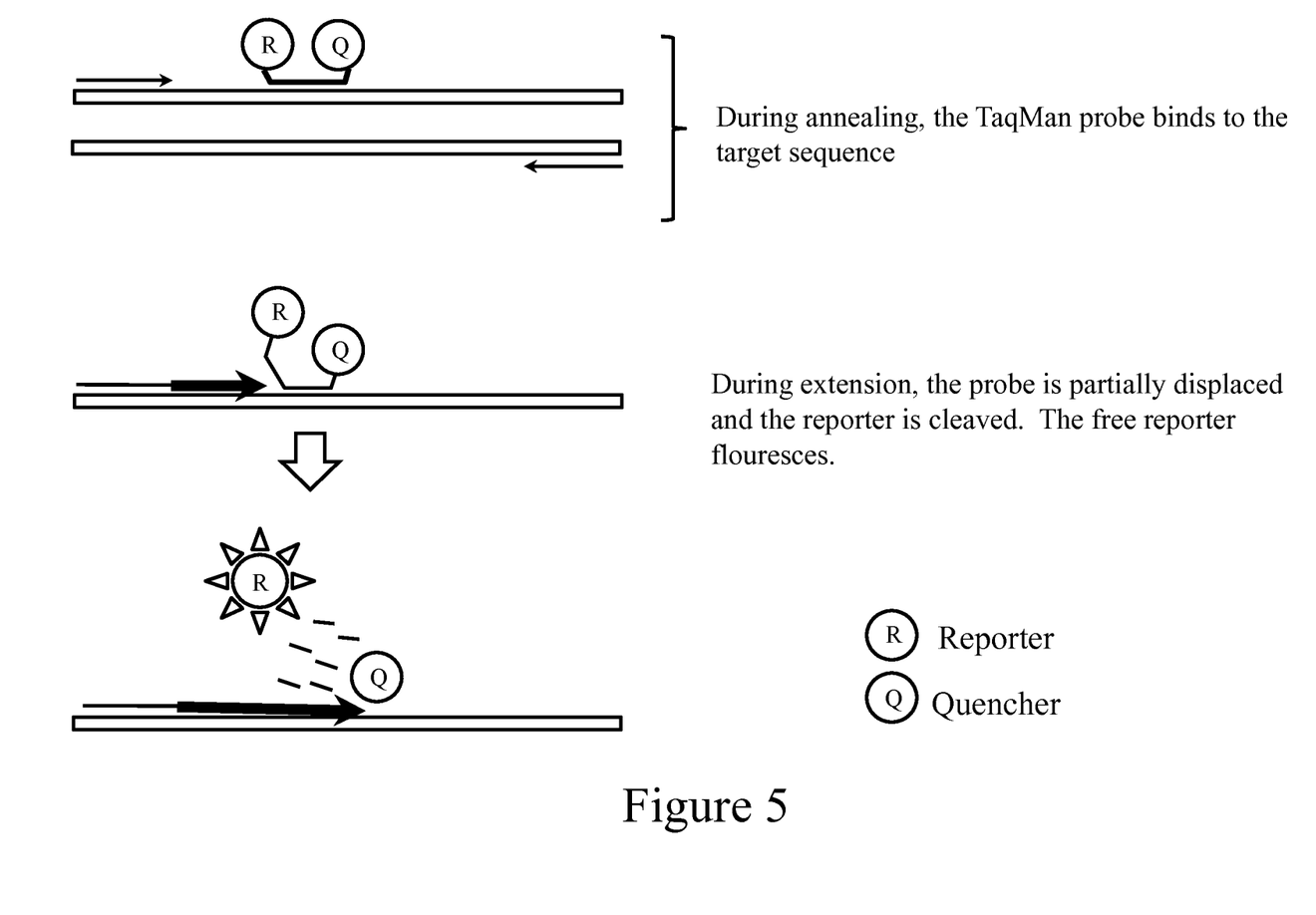
FIG. 5 shows how the TAQMAN reporter binds during the annealing step, but is displaced and cleaved during the extension step.

FIG. 5 shows how TAQMAN probes are hydrolyzed by Taq polymerase. More specifically, when intact, the fluorescence of the reporter is quenched due to its proximity to the quencher (see FIG. 5). The amplification reaction includes a combined annealing/extension step during which the probe hybridizes to the target and the dsDNA-specific 5'→>3' exonuclease activity of Taq or Tth cleaves off the reporter. As a result, the reporter is separated from the quencher, resulting in a fluorescent signal that is proportional to the amount of amplified product in the sample.

Although not wanting to be bound by theory, the main advantages of using TAQMAN probes include high specificity, a high signal-to-noise ratio, and the ability to perform multiplex reactions. The disadvantages are that the initial cost of the probe may be high and the assay design may not be trivial. One of ordinary skill in the art understands that the design of TAQMAN probes may vary, but are considered to be within the spirit and scope of the invention.

This bed bug detection kit can be used as a tool to detect emerging bed bug infestations before clinical symptoms are noticed. For example, when bed bugs grow from egg to adult they shed the DNA-containing egg and later a DNA-containing exoskeleton. This invention may be particularly helpful for hotel or hospital operations as part of a routine scheduled maintenance plan for the detection of a few bed bugs before an infestation has a chance to emerge. Specific PCR probes have been designed to detect minute quantities of DNA from the general family of bed bug organisms known as Cimicidae. The detection can be determined directly in bed-bug-DNA-containing dust samples collected from beds, carpets, clothes, or almost any suspect surface in a room or area that is suspected of having bed bugs.

The analysis can be general family or species-specific. Sample collection takes approximately one minute or less, and for multiple areas can take as little as 5 minutes. The samples are sent to an offsite laboratory, and determination of the presence/absence of bed bugs can be obtained within 24 hours. One having ordinary skill in the art will understand the importance of detecting an emerging bed bug infestation early using this simple and efficient Bed Bug DNA Detection Kit.

How Real Time PCR Works to Detect Bed Bugs.

Bed bugs have a life cycle that includes growing from an egg→larval→adult. During that time bed bugs from the general family of organisms known as Cimicidae shed their exoskeleton and leave fecal droppings that contain residual genetic clues of an infestation. A swab or functional equivalent thereof is used to collect dust from bedding, carpeting, upholstery, surrounding furniture, piles of books, papers, linens, bedding frames, nightstands, or any additional areas suspected of bed bugs. The collected particulate matter is dissolved and DNA is extracted from the sample. A set of Cimicidae species-specific primers and fluorescent probes are used to amplify DNA from the collected samples by real-time PCR, wherein the amplification products are detected by the computer instrumentation and/or gel electrophoresis. The species-specific *Cimex lectularius* primers and probe have been tested against closely related species and other common household insects with specific and reproducible results for *Cimex lectularius* DNA. Using the real-time PCR kit and protocol described herein, the detection of <5 µg of bed bug material can be visualized per 100 mg of extracted dust. The presence/absence data of bed bug DNA for the tested area(s) yield either: (a) a positive result indicating that bed bug DNA was present in the sample; or (b) a negative result indicating that the sample did not contain any bed bug DNA.

Figure 1:
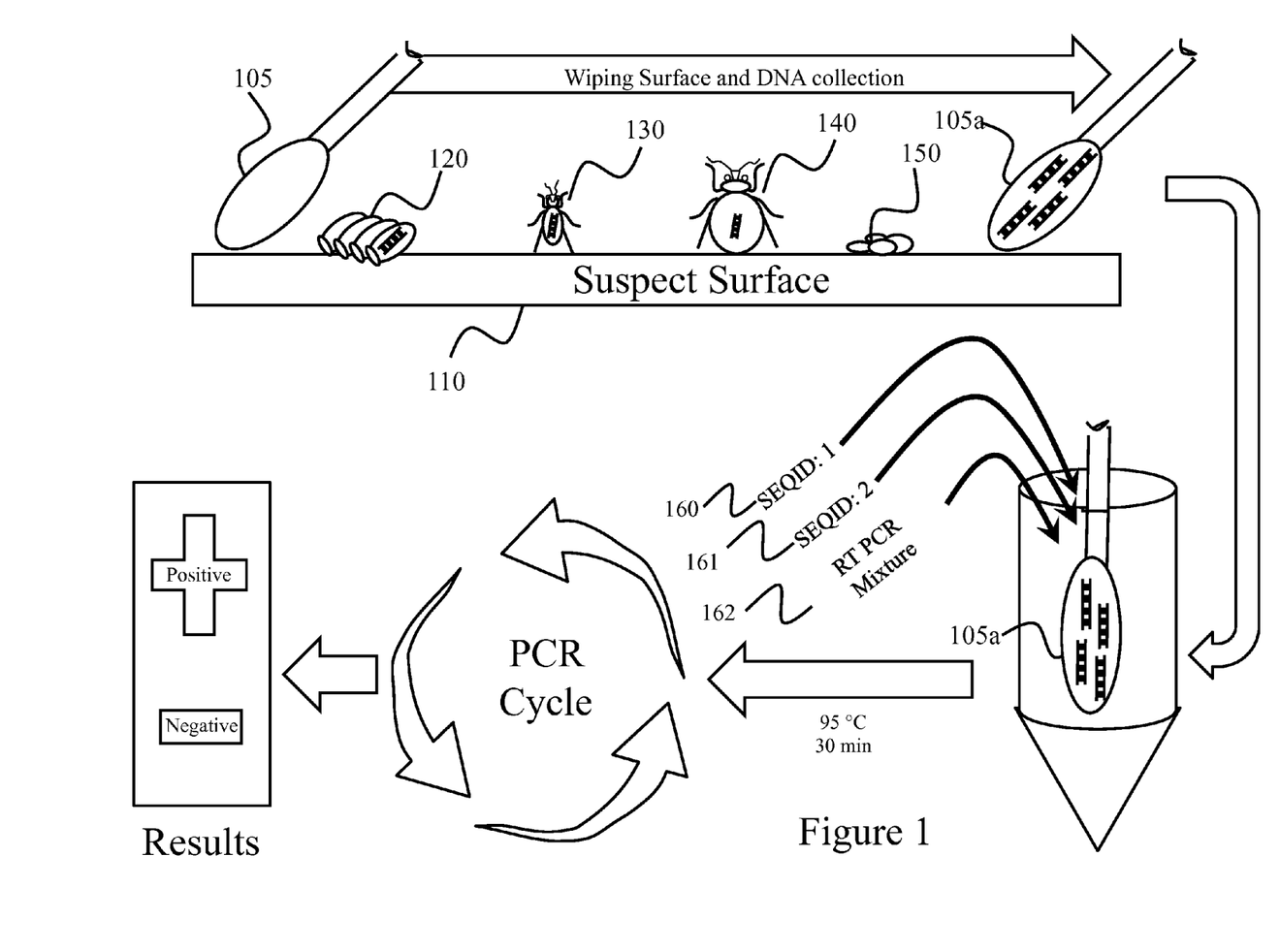
FIG. 1 shows an illustration of the kit components and method of detecting bed bugs.

One embodiment of the invention is a bed bug detection kit and method of using the kit. The method used to detect the presence of bed bugs at a suspect location is illustrated in FIG. 1. More specifically, a sterile swab, free from bed bug DNA (105), is used to collect DNA samples from one or more suspect surface(s) (110). The suspect surface (110) may contain: bed bug eggs or egg remnants thereof (120); bed bug larva, larval exoskeletons, or remnants thereof (130); bud bugs, bed bug exoskeletons or remnants thereof (140); or bed bug droppings, saliva, or any bed bug macro particles containing bed bug DNA thereof (150). One aspect of the current invention involves a user contacting the swab (105) with one or more suspect surface(s) (110) using a motion capable of collecting residual bed bug nucleic acid samples. Once the swab has contacted the suspect surface, the swab may (105a) or may not contain nucleic acid samples of bud bugs.

The presence of bed bug nucleic acid can be detected using one or more PCR techniques. Generally, a swab that has contacted a suspect surface and contains dust, dander, hair, pollen, or other environmental debris in addition to the bed bug DNA. This DNA containing swab is placed into a tube containing about 500 µl of TE buffer and agitated vigorously for 30 seconds to wash the swabs and collect the particular matter off from the swabs. The tubes are then mixed using a vortex mixer for about 15 to 30 seconds then heated at approximately 65° C. for about 15 minutes, and followed by another 15-30 second mix using a vortex mixer generating the mixed tubes. The mixed tubes are subjected to centrifugation at about 14,000 rpm for about 3 minutes for the purpose of removing any non-soluble debris forming a centrifugal solution (note: this step can be optional). Following centrifugation some of the supernatant can be collected and used in one of several possible DNA extraction protocols. In a preferred embodiment about 200 µl of the supernatant is placed into about 500 µl of DNA Extraction Solution (note: The QUICK EXTRACT DNA EXTRACTION Solution 1.0 from Epicentre Biotechnologies was used). The resulting composition is mixed for about 15 seconds using a vortex mixer, incubated at 98° C. for about 10 minutes, and then mixed using a vortex mixer for an additional about 15 seconds, and then subjected to centrifugation for about 3 minutes at about 14,000 rpm for the purpose of removing non-soluble components from the Extracted DNA supernatant. The Extracted DNA Supernatant can be removed and is now ready for PCR amplification or may be stored at 4° C. until ready for use.

One of ordinary skill in the art will understand that general DNA isolation is a routine procedure to collect DNA for subsequent molecular or forensic analysis. Although not wanting to be bound by theory, there are three basic and one optional steps in a DNA extraction:

Breaking the cells open, commonly referred to as cell disruption or cell lysis, to expose the DNA within. This is commonly achieved by grinding or sonicating the sample.

Removing membrane lipids by adding a detergent.

Removing proteins by adding a protease (optional but almost always done).

Precipitating the DNA with an alcohol, usually ice-cold ethanol or isopropanol. Since DNA is insoluble in these alcohols, it will aggregate together, giving a pellet upon centrifugation. This step also removes alcohol-soluble salt.

Refinements of the technique include adding a chelating agent to sequester divalent cations such as $Mg^{2+}$ and $Ca^{2+}$, which prevents enzymes like DNAse from degrading the DNA.

Cellular and histone proteins bound to the DNA can be removed either by adding a protease or by having precipitated the proteins with sodium or ammonium acetate, or extracted them with a phenol-chloroform mixture prior to the DNA-precipitation.

One of ordinary skill in the art understand that there are various types of nucleic acid amplification techniques available and all are considered to be within the spirit and scope of the invention. In molecular biology, real-time polymerase chain reaction, also called quantitative real time polymerase chain reaction (Q-PCR/qPCR/qrt-PCR) or kinetic polymerase chain reaction (KPCR), is a laboratory technique based on the PCR, which is used to amplify and simultaneously quantify a targeted DNA molecule. For one or more specific sequences in a DNA sample, Real Time-PCR enables both detection and quantification. The quantity can be either an absolute number of copies or a relative amount when normalized to DNA input or additional normalizing genes.

The procedure follows the general principle of polymerase chain reaction; its salient feature is that the amplified DNA is detected as the reaction progresses in real time. This is an approach compared to standard PCR, where the product of the reaction is detected at its end. Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

Frequently, real-time PCR is combined with reverse transcription to quantify messenger RNA and Non-coding RNA in cells or tissues. Abbreviations used for real-time PCR methods vary widely and include: RTQ-PCR, Q-PCR or qPCR. Real-time reverse-transcription PCR is often denoted as: qRT-PCR, RRT-PCR, or RT-rt PCR. The acronym "RT-PCR" commonly denotes reverse-transcription PCR and not real-time PCR, but not all authors adhere to this convention.

Fluorescent reporter probe method is the preferred method for all samples/testing. More specifically, the "TAQ-MAN probe technology" is preferred, and a sample collected from a bed bug colony is used as a positive control.

Figure 4:
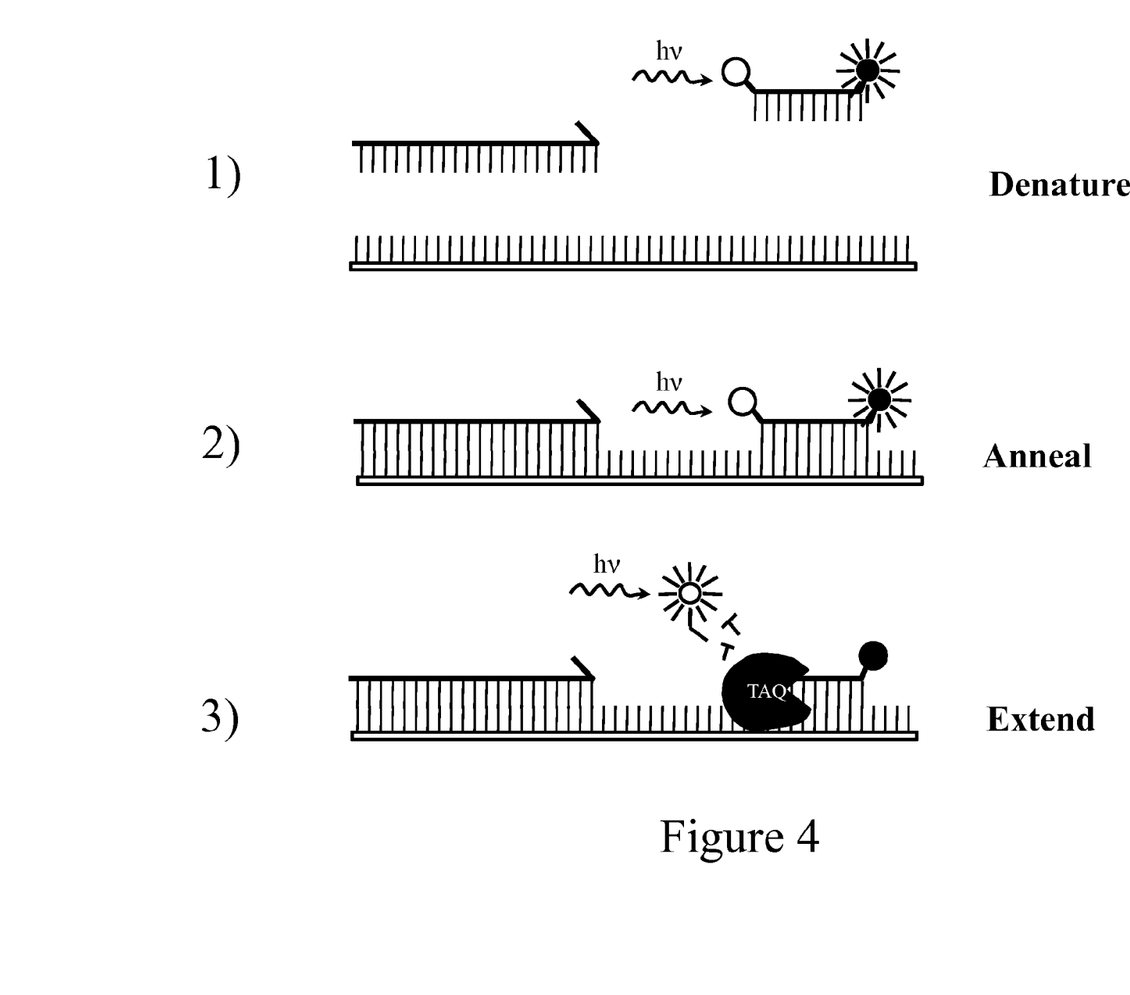
FIG. 4 shows how a reporter and quencher marked prove can be used to amplify a gene of interest.

Referring to FIG. 4 Panel (1) shows the intact probe's, reporter fluorescence is quenched. Panel (2) shows probes and the complementary DNA strand are hybridized and reporter fluorescence is still quenched. Panel (3) shows that during PCR, the probe is degraded by the Taq polymerase and the fluorescent reporter released.

Fluorescent reporter probes detect only the DNA containing the probe sequence. Although not wanting to be bound by theory, the use of the reporter probe significantly increases specificity, and enables quantification even in the presence of non-specific DNA amplification. Fluorescent probes can be used in multiplex assay for detection of several genes in the same reaction based on specific probes with different-colored labels, provided that all targeted genes are amplified with similar efficiency. The specificity of fluorescent reporter probes also prevents interference of measurements caused by primer dimers, which are undesirable potential by-products in PCR. However, fluorescent reporter probes do not prevent the inhibitory effect of the primer dimers, which may depress accumulation of the desired products in the reaction.

The method relies on a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the Taq polymerase breaks the reporter-quencher proximity and thus allows unquenched emission of fluorescence, which can be detected after excitation with a laser. An increase in the product targeted by the reporter probe at each PCR cycle therefore causes a proportional increase in fluorescence due to the breakdown of the probe and release of the reporter.

The PCR is prepared as usual, and the reporter probe is added. As the reaction commences, during the annealing stage of the PCR both probe and primers anneal to the DNA target. Polymerisation of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in the real-time PCR thermocycler, and its geometric increase corresponding to exponential increase of the product is used to determine the threshold cycle (CT) in each reaction.

The real-time PCR amplification reaction mixture is prepared. For example, a 50 µl real-time PCR amplification reaction mixture comprises: about 5 µl of the Extracted DNA Supernatant to detect template DNA; 25 µl of Master Mix (note: contains Contains 2× reaction buffer with dNTPs, iTaq DNA polymerase, 6 mM MgCls and stabilizers from Bio-Rad (catalog #170-886), (162)), 1 µl of SEQID No. 1 (i.e. Forward Primer (160)); 1 µl of SEQID No. 2 (i.e. Reverse Primer 161)); 1 µL of probe (SEQID No. 3) and 17 µl of DNAse/RNAse free $H_2O$.

The 50 µl real-time PCR amplification reaction mixture is thoroughly mixed and subjected to real-time PCR amplification protocols. In a preferred embodiment, utilization of more than one sample is used. For example, one or more samples may be loaded into a standard 96 well plate, wherein the plate is covered with real-time PCR optically clear sealing tape and then placed into a Bio-Rad I-cycler IQ Multi-Color Real Time PCR detection system (Bio-Rad Life Science Research, 2000 Alfred Nobel Drive, Hercules, Calif. 94547, 1-800-424-6723). The thermal cycling protocol comprises: an initial melting cycle of 95° C. for 3 minutes; a first step denaturing cycle having 94° C. degrees for 15 seconds; a second step annealing cycle of 53° C. for 20 seconds; and a third step primer extension cycle of 53° C. for 30 seconds. In a preferred embodiment the first step; second step; and third step are repeated for 40 cycles and the mixture is then returned to about room temperature, or about 25° C. The test always includes a positive control of confirmed bed bug DNA and a negative control of no DNA to ensure test accuracy. The results are visualized as either being Positive for bed bug DNA or Negative for bed bug DNA using the corresponding iCycler software program supplied from Bio-Rad for measurement and quantification of products. Alternatively, validation can be performed by visual observation using gel electrophoresis on a 4:1 agarose gel (Note: Reliant Gel System 4% NuSieve 3:1 Plus Agarose Gels Cat #54929 from Lonza Inc. Rockland, Me. USA 207-594-3400). Positive products produce a visual band of 92 base pairs after bring subjected to 115 volts for 40 minutes.

Example 2

Real-Time PCR and Traditional PCR

The invention described herein is capable of utilizing both real-time PCR and traditional PCR. One having ordinary skill in the art will appreciate that there are limitations of traditional PCR when compared to real-time PCR. For example, real-time chemistries allow for the detection of PCR amplification during the early phases of the reaction. Measuring the kinetics of the reaction in the early phases of PCR provides a distinct advantage over traditional PCR detection. Traditional methods use Agarose gels for detection of PCR amplification at the final phase or end-point of the PCR reaction, which is very time consuming and many results may vary based on size discrimination, which is not exact. In contrast, real-time PCR is sensitive enough to precisely detect these changes in size discrimination. Additionally, agarose gel resolution is very poor, about 10 fold. Real-Time PCR can distinguish as little as a two-fold change in quantity.

One of ordinary skill in the art understands the intricacies of the PCR phases and would realize that some end-point PCR reaction conditions may need to be modified without departing from the spirit and scope of the present invention. Although not wanting to be bound by theory, one of ordinary skill in the art understands that a basic PCR run can be broken up into three phases:

(1) Exponential: Exact doubling of product is accumulating at every cycle (assuming 100% reaction efficiency). The reaction is very specific and precise;

(2) Linear (High Variability): The reaction components are being consumed, the reaction is slowing, and products are starting to degrade.

(3) Plateau (End-Point Gel detection for traditional methods): The reaction has stopped, no more products are being made and if left long enough, the PCR products may begin to degrade.

One having ordinary skill in the art understands that DNA amplification can be visualized differently to assess the PCR phases, wherein these modifications would not be considered to deviate from the spirit and scope of the invention. Although not wanting to be bound by theory, there is a quantitative relationship between amount of starting target sample and amount of PCR product at any given cycle number. Real-Time PCR detects the accumulation of amplicon during the reaction. The data is then measured at the exponential phase of the PCR reaction. Traditional PCR methods use Agarose gels or other post PCR detection methods, which are not as precise. The exponential phase is the optimal point for analyzing data. Although not wanting to be bound by theory, Real-Time PCR makes quantitation of DNA and RNA easier and more precise than other methods, but is not the only way to utilize this invention.

One of ordinary skill in the art will be familiar with PCR reaction utilizing a 5' exo-nuclease activity of Taq Polymerase with FRET (Fluorescent Resonant Energy Transfer), which makes it possible to detect PCR amplification in Real-Time. As shown in FIG. 4, a general reporter and quencher marker can be used to amplify and detect a gene of interest in real time. In a more specific example, FIG. 5 shows how the TAQMAN reporter binds during the annealing step, but is displaced and cleaved during the extension step. The 5'exo-nuclease activity of the enzyme acts upon the surface of the template to remove obstacles downstream of the growing amplicon that may interfere with its' generation. The principle of FRET and the 5' exo-nuclease activity is that when a high-energy dye is in close proximity to a low-energy dye, there will be a transfer of energy from high to low. One of ordinary skill in the art can design DNA amplification primers having a high-energy dye termed a Reporter at the 5' end, and a low-energy molecule termed a Quencher at the 3' end. When this probe is intact and excited by a light source, the Reporter dye's emission is suppressed by the Quencher dye as a result of the close proximity of the dyes. However, when the probe is cleaved by the 5' nuclease activity of the enzyme, the distance between the Reporter and the Quencher increases causing the transfer of energy to stop. The fluorescent emissions of the reporter increase and the quencher decrease. The increase in reporter signal is captured by the Sequence Detection instrument and displayed by the software. Similar probe designs are available that would not depart from the spirit and scope of the invention.

Figure 2:
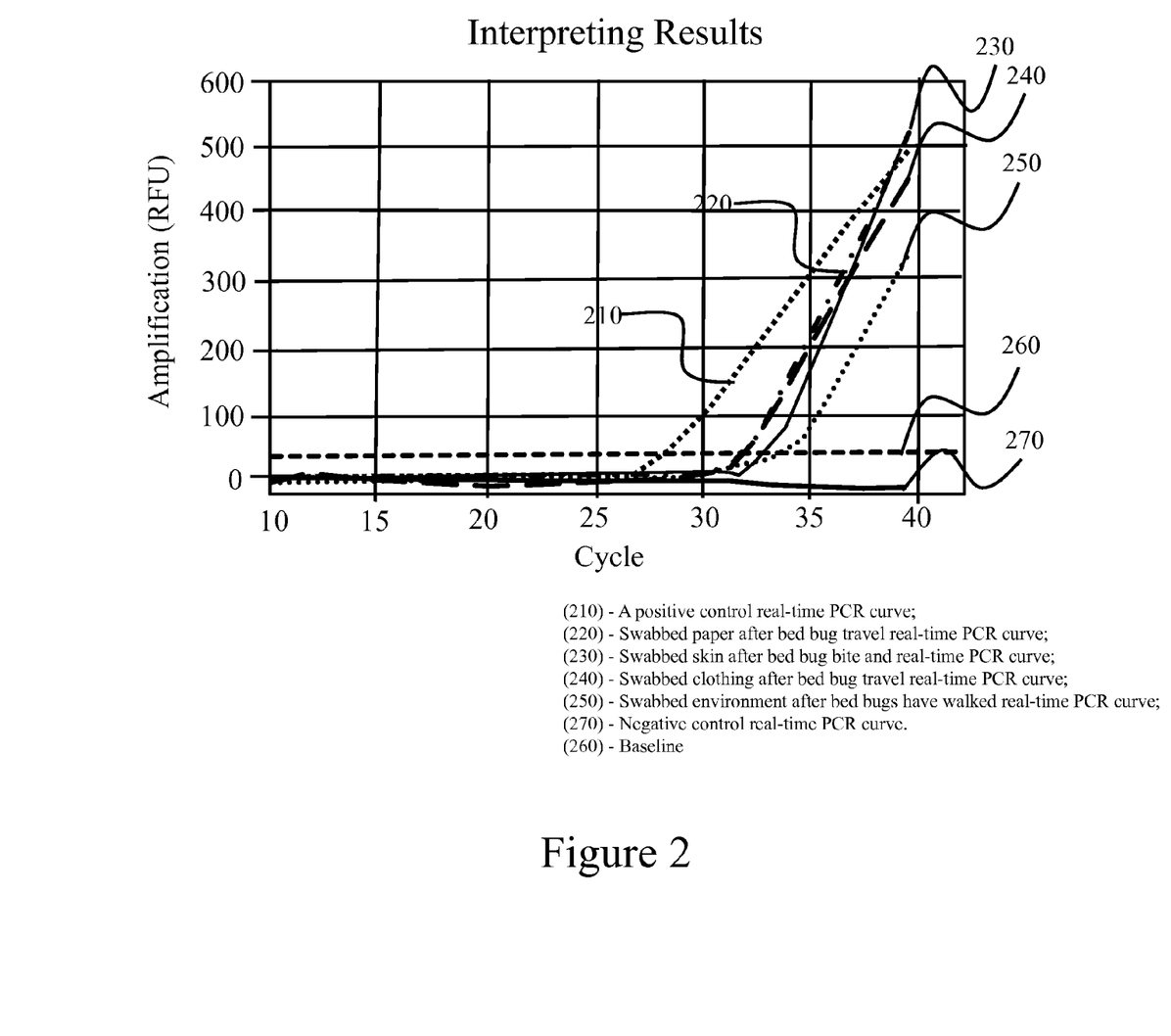
FIG. 2 shows an amplification graph of various samples and controls that have been exposed to bed bug DNA.
Figure 3:
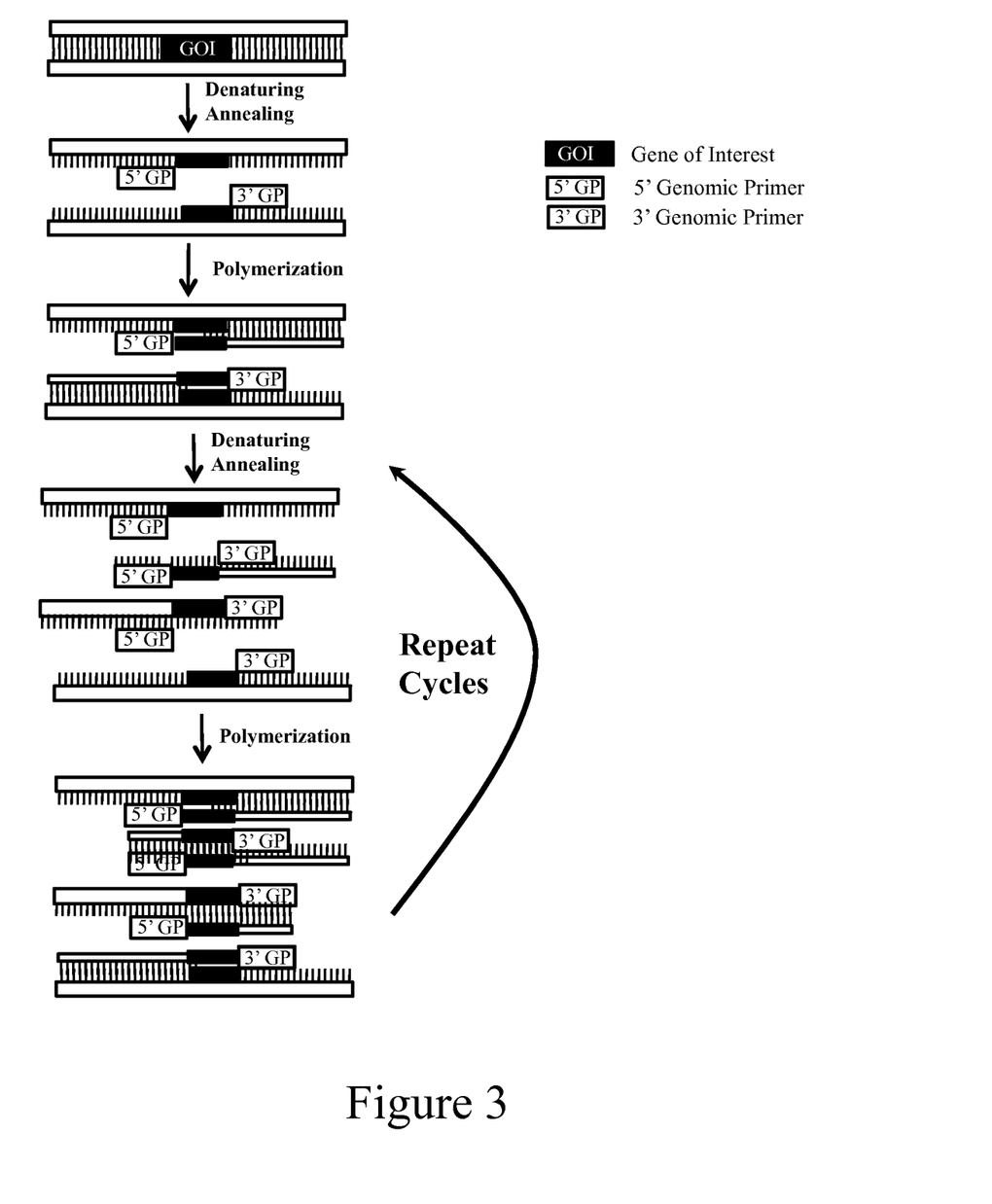
FIG. 3 shows how a gene of interest can be PCR amplified using a 5' Genomic Primer and a 3' Genomic Primer.

FIG. 2 shows a positive control real-time PCR curve (210); swabbed paper after bed bug travel real-time PCR curve (220); swabbed skin after bed bug bite and real-time PCR curve (230); swabbed clothing after bed bug travel real-time PCR curve (240); swabbed environment after bed bugs have walked real-time PCR curve (250); negative control real-time PCR curve (270); baseline (260).

Figure 6:
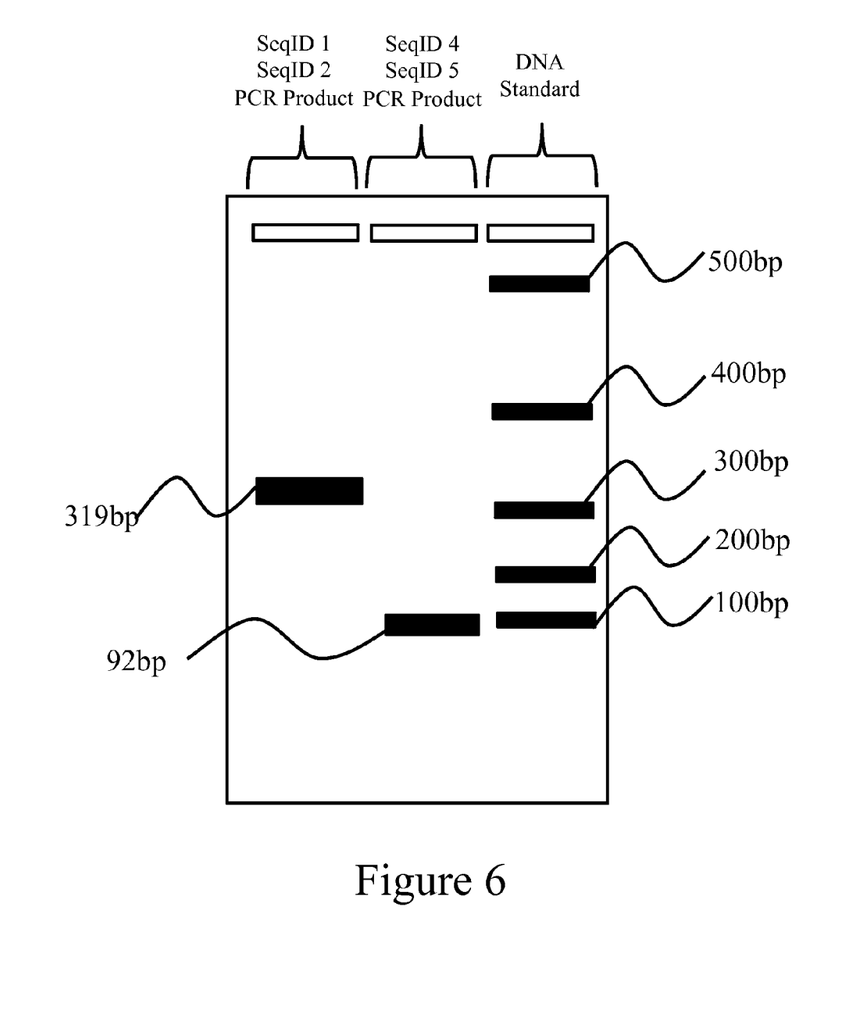
FIG. 6 shows an illustration of a the traditional PCR products from SEQID No.: 1 and SEQID No.: 2 having a 92 bp amplification product, and SEQID No.: 4 and SEQID No.: 5 having a 319 bp amplification product.

In addition to the sensitive real time PCR, FIG. 6 shows an illustration of how a the traditional PCR products from SEQID No.: 1 and SEQID No.: 2 having a 92 bp amplification product, and SEQID No.: 4 and SEQID No.: 5 having a 319 bp amplification product.

REFERENCES CITED

The entire content of each of the following U.S. patent documents and published references are hereby incorporated by reference.

U.S. PATENT DOCUMENTS

| U.S. Pat. No. | Title |
|---|---|
| 4,683,202 | Process for amplifying nucleic acid sequences |
| 7,880,060 | Insecticidal polynucleotides and methods of use thereof |
| 7,812,219 | Compositions and methods for control of insect infestations in plants |
| 6,750,256 | Use of aromatic aldehydes as insecticides |
| 5,839,224 | Aromatic aldehydes as insecticides and for killing arachnids |
| 5,792,467 | Repellent compositions containing aromatic aldehydes |
| 5,723,440 | Controlling hemipteran insect pests with *Bacillus thuringiensis*. |
| 4,683,195 | Process for amplifying, detecting, and/or-cloning nucleic acid sequences having Kary B. Mullis et al., listed as inventors. |
| 5,455,166 | Strand displacement amplification, having George T. Walker listed as inventor. |
| 5,409,818 | Nucleic acid amplification process, having Cheryl Davey et al., listed as inventors. |
| 4,458,006 | Photopolymerizable mixture and photopolymerizable copying material prepared, having Reinhard Donges et al., listed as inventors. |

What is claimed is:

1. A composition comprising:
   a. a forward primer comprising SEQ ID NO: 1;
   b. a reverse primer comprising SEQ ID NO: 2;
   c. a probe comprising SEQ ID NO: 3 and the probe is labeled with a fluorescent chemistry marker; and
   d. a sample collected from an area suspected of harboring at least one member of the family of Cimicidae lectularius;
   wherein the composition is used for visualizing the fluorescent chemistry marker during a PCR amplification cycle when a non-naturally occurring fluorescent amplicon is generated from a Cimicidae-DNA sample collected from the area together with the forward primer, the reverse primer, the probe, in the presence of a PCR reaction buffer, a thermostable PCR polymerase and dNTP's, and the amplicon will not be generated in the absence of Cimicidae-DNA.

2. The composition of claim 1, wherein the probe labeled with the fluorescent chemistry marker is a probe having a hairpin shaped molecule with an internally quenched fluorophore whose fluorescence is restored when it binds to a target nucleic acid sequence.

3. The composition of claim 1, wherein the probe labeled with a fluorescent chemistry marker is a hydrolysis probe having a fluorophore covalently attached to a 5'-end of the probe and a quencher at a 3'-end.

4. The composition of claim 1, further comprising (e) a positive-control-Cimicidae DNA template for confirming the Cimicidae-PCR amplicon is generated.

5. The composition of claim 1, further comprising (f) the thermostable PCR polymerase.

6. The composition of claim 1, further comprising (g) dNTP's.

7. A method comprising the steps of:
   (a) collecting a test sample from an environment exposed to at least one member of a family of Cimicidae organisms;
   (b) amplifying a Cimicidae-DNA-sample using a PCR amplification reaction to produce a non-naturally occurring amplicon of Cimicidae DNA, wherein a forward PCR primer having SEQ ID No. 1 and a reverse PCR Primer having SEQ ID No. 2, are hybridized to the cimicidae-DNA-sample and used to generate the non-naturally occurring amplicon; wherein SEQ ID NO: 3 is conjugated to a signal generating compound that is capable of producing a fluorescent signal during the PCR amplification reaction to produce the non-naturally occurring amplicon of Cimicidae DNA;
   (c) detecting the fluorescent signal following producing the fluorescent signal during the PCR amplification the non-naturally occurring amplicon of Cimicidae DNA; and
   (d) determining the presence the Cimicidae organism by having the fluorescent signal detection of the non-naturally occurring amplicon above background levels;
   wherein the method steps are used for determining the presence of Cimicidae-DNA from an environment exposed to at least one member of a family of Cimicidae organisms and the fluorescent signal will not be generated in the absence of Cimicidae-DNA.

* * * * *

SEQUENCE LISTING

```
<160> NUMBER OF SEQ ID NOS: 5

<210> SEQ ID NO 1
<211> LENGTH: 17
<212> TYPE: DNA
<213> ORGANISM: artificial sequence
<220> FEATURE:
<223> OTHER INFORMATION: 5' Forward Primer (17-mer)

<400> SEQUENCE: 1
tcgcattgac cgcgtag                                                  17

<210> SEQ ID NO 2
<211> LENGTH: 17
<212> TYPE: DNA
<213> ORGANISM: artificial sequence
<220> FEATURE:
<223> OTHER INFORMATION: 3? Reverse Primer (17 mer)

<400> SEQUENCE: 2
acggtacttc ggacgga                                                  17

<210> SEQ ID NO 3
<211> LENGTH: 20
<212> TYPE: DNA
<213> ORGANISM: artificial sequence
<220> FEATURE:
<223> OTHER INFORMATION: Fluorescent Probe (15 mer)

<400> SEQUENCE: 3
tgtggaccca ggccgtccga                                               20

<210> SEQ ID NO 4
<211> LENGTH: 22
<212> TYPE: DNA
<213> ORGANISM: artificial sequence
<220> FEATURE:
<223> OTHER INFORMATION: 5' Forward Primer Cimicidae(22-mer)

<400> SEQUENCE: 4
ctgtgcaaag gtagcataat aa                                            22
```

```
<210> SEQ ID NO 5
<211> LENGTH: 30
<212> TYPE: DNA
<213> ORGANISM: artificial sequence
<220> FEATURE:
<223> OTHER INFORMATION: 3' Reverse Primer (30-mer)

<400> SEQUENCE: 5
ccttaagtaa cttaaactta taatcaaaac                                    30
```